United States Patent [19]

Engelstad et al.

[11] Patent Number: 4,909,257

[45] Date of Patent: Mar. 20, 1990

[54] METHOD FOR ATTAINING IN VIVO TISSUE-SPECIFIC CONTRAST BY NUCLEAR MAGNETIC RESONANCE IMAGING

[75] Inventors: Barry L. Engelstad, Orinda, Calif.; Robert C. Brasch; Robert S. Hattner, both of Mill Valley; George Wesbey, Mercer Island; John P. Huberty, Corte Madera, Calif.

[73] Assignee: The Regents of the University of California, Oakland, Calif.

[21] Appl. No.: 346,346

[22] Filed: Apr. 28, 1989

Related U.S. Application Data

[63] Continuation of Ser. No. 858,607, May 1, 1986, abandoned, which is a continuation-in-part of Ser. No. 488,733, Apr. 26, 1983, abandoned.

[51] Int. Cl.⁴ ............................................. A61B 6/00
[52] U.S. Cl. ..................................... 128/654; 128/659; 424/9
[58] Field of Search ............................... 128/654–659; 424/2, 4, 9; 435/4

[56] References Cited

U.S. PATENT DOCUMENTS

| | | | |
|---|---|---|---|
| 4,352,751 | 10/1982 | Weider et al. | 435/4 |
| 4,454,106 | 6/1984 | Granson et al. | 128/659 |
| 4,647,447 | 3/1987 | Gries et al. | 424/2 |

OTHER PUBLICATIONS

Pykett, I., "NWR Imagining in Medicine," *Scientific Am.* vol. 246, No. 5, 5/82, pp. 78–88.

Primary Examiner—C. Fred Rosenbaum
Assistant Examiner—Sharon Rose
Attorney, Agent, or Firm—Flehr, Hohbach, Test, Albritton & Herbert

[57] ABSTRACT

A method is provided for obtaining in vivo diferentiation of tissues in an animal by nuclear magnetic resonance imaging comprising the steps of introducing into the animal a complex comprising a paramagnetic ferric ion and a chelator. Particular contrast agents, Fe(HBED) and Fe(EHPG), are excretable by a hepatobiliary pathway.

4 Claims, 2 Drawing Sheets

METHOD FOR ATTAINING IN VIVO TISSUE-SPECIFIC CONTRAST BY NUCLEAR MAGNETIC RESONANCE IMAGING

This is a continuation of application Ser. No. 858,607, filed May 1, 1986, which is a continuation-in-part of Ser. No. 488,733, filed Apr. 26, 1983, both of which are abandoned.

The present invention is directed to a method of in vivo non-invasive diagnostic imaging by the technique of NMR imaging utilizing chelated paramagnetic metal ions as contrast agents. The present invention is particularly directed to a method utilizing chelated ferric ions which are tissue-specific NMR imaging contrast agents.

The non-invasive in vivo diagnostic technique of NMR imaging has been utilized to produce cross-sectional images of living subjects without exposure to harmful ionizing radiation, as described, for example, by Hansen et al *Radiology*, 136: 695-700 (1980). An NMR imaging apparatus has been developed wherein cross-sectional NMR images of selected regions and various tissues within a living animal may be taken, as described by Crooks et al, *Radiology*, 136: 701-706 (1980).

An important principle of NMR imaging is that the spin-lattice (T1) and spin-spin (T2) magnetic relaxation times of various tissues often inherently differ. The values of T1 and T2 are the exponential time constants describing the rates with which hydrogen nuclei within a static magnetic field equilibrate. These rate constants depend on the physical environment, such as, temperature, viscosity, the external magnetic field strength and internal magnetic forces. Among the stable nuclei, hydrogen, which is the most abundant nucleus in the body, is the most useful for NMR imaging.

An important aspect of NMR imaging is its non-hazardous nature. The clinically used magnetic field strength and radio frequency levels of NMR produce no known physiological danger. See Budinger, *IEEE Trans. Nucl. Sci.* NS-26: 2821-2825 (1979). However, a limitation of NMR imaging is that only a fixed unit of contrast differentiation between certain pathologic and normal anatomic tissees may be obtainable. Thus, a means for increasing the NMR signal from selected tissues and organs is desirable to improve the observed contrast from surrounding tissues and organs. Therefore, there is a need for contrast agents in NMR imaging which increase the inherent contrast (i.e., difference in density) between different tissues or different regions of the same tissue as recorded by the imaging system. Such contrast agents as stable-free nitroxide radicals and manganese ion, have been used due to their paramagnetic nature. The effect of administered paramagnetic ions is chiefly to shorten both T1 and T2. The effect is concentration-dependent and generally follows the pattern following when the concentration of the paramagnetic ions increases: intensity initially increases due to the predominant effect of T1 shortening. At higher concentrations of the paramagnetic ions, intensity decreases due to the predominant effect of T2 shortening. However, in the continuing search for NMR imaging contrast agents, there is a difficulty in devising contrast agents which also meet other physiological criteria, such as being non-toxic to the animal and being excretable from the body.

An important objective of NMR imaging is to improve diagnostic sensitivity by spatially discriminating among tissues which may have inherently similar NMR characteristics. This light be achieved by developing contrast agents which show different pharmaceutical uptake among different tissues. In addition, the nature of the pharmaceutical uptake may improve the diagnostic specificity. Image intensity and relaxation times of some tissues and of some tumors have considerable overlap with similar parameters of other normal tissues, therefore, spatial discrimination of juxtaposed organs of similar intensity and/or of normal and abnormal tissues, is frequently not possible. Furthermore, it is inherent that NMR properties of tissue bear either no relationship, or at best an indirect relationship, to parameters of the organ function.

Therefore it would be desirable to provide available NMR contrast agents which exhibit in vivo selective incorporation to permit refined distinction between various normal tissues, and/or to improve lesion detection and characterization, and/or to provide information regarding organ function.

There is a particular need in this regard for an NMR contrast agent which will afford the ability to selectively enhance the liver and biliary tree by clearance of lipophilic compounds through hepatobiliary rather than renal excretion. It is believed that heretofore there has been no such reagent developed which has shown to satisfactorily fulfill this function.

While most forms of NMR imaging are based on the proton, i.e., its abundance, its motion, and its local physiochemical environment, these parametrrs which are measured are largely instrumental parameters, based on magnetic field strength and pulse sequence, rather than on intrinsic NMR properties of the tissue being studied. One type of pulse sequence, spin echo imaging, however, is particularly effective for lesion detection. There is a mathematical relationship between image intensity as detected by spin echo imaging and the intrinsic NMR properties, proton density, proton motion,, the proton relaxation times, T1 and T2. These properties are responsible for some aspect of tissue contrast, however the physicochemical environment (as reflected by T1 and T2) is responsible for rather great changes and can dominate tissue characterization and diagnosis. Factors such as free or bound water concentration, pH, protein concentration, ionic strength, temperature and paramagnetic influences modulate the image intensity through T1 and T2. Factors that shorten T1 or lengthen T2 increase the spin echo image intensity while factors that lengthen T1 or shorten T2 decrease the image intensity.

One of the ways to affect a physicochemical environment is by paramagnetic relaxation. Paramagnetic substances are characterized by the presence of unpaired electrons that produce magnetic moments greatly exceeding that of the proton. Paramagnetic substances interact with nuclei, including hydrogen, to promote relaxation. Paramagnetic compounds are advantageous to enhance NMR contrast because only small amounts are needed (less than 0.01 to 1.0 mM), there is a flexibility in designing the agents, in most cases special instrumentation is not required, and there is a diagnostic benefit.

While many paramagnetic materials are possible, heretofore literature on NMR contrast agents reflects that much effort in the field has been directed toward nitroxides, lanthanons and other transition metals such as manganese and chromium, all of which have little or no precedent for medical use. It has been found, surprisingly, under the present invention however that a certain group of iron chelates is efficacious and versatile compared to other paramagnetic compounds and may be among the safest and therefore the most adaptable for early clinical use.

It is, therefore, an object of the present invention to provide an improved method for in vivo NMR imaging utilizing paramagnetic chelated metal ions as contrast agents, particularly chelated ferric ions.

These and other objects will be readily apparent to those of ordinary skill in the art from the following description and claims.

Figure 1:
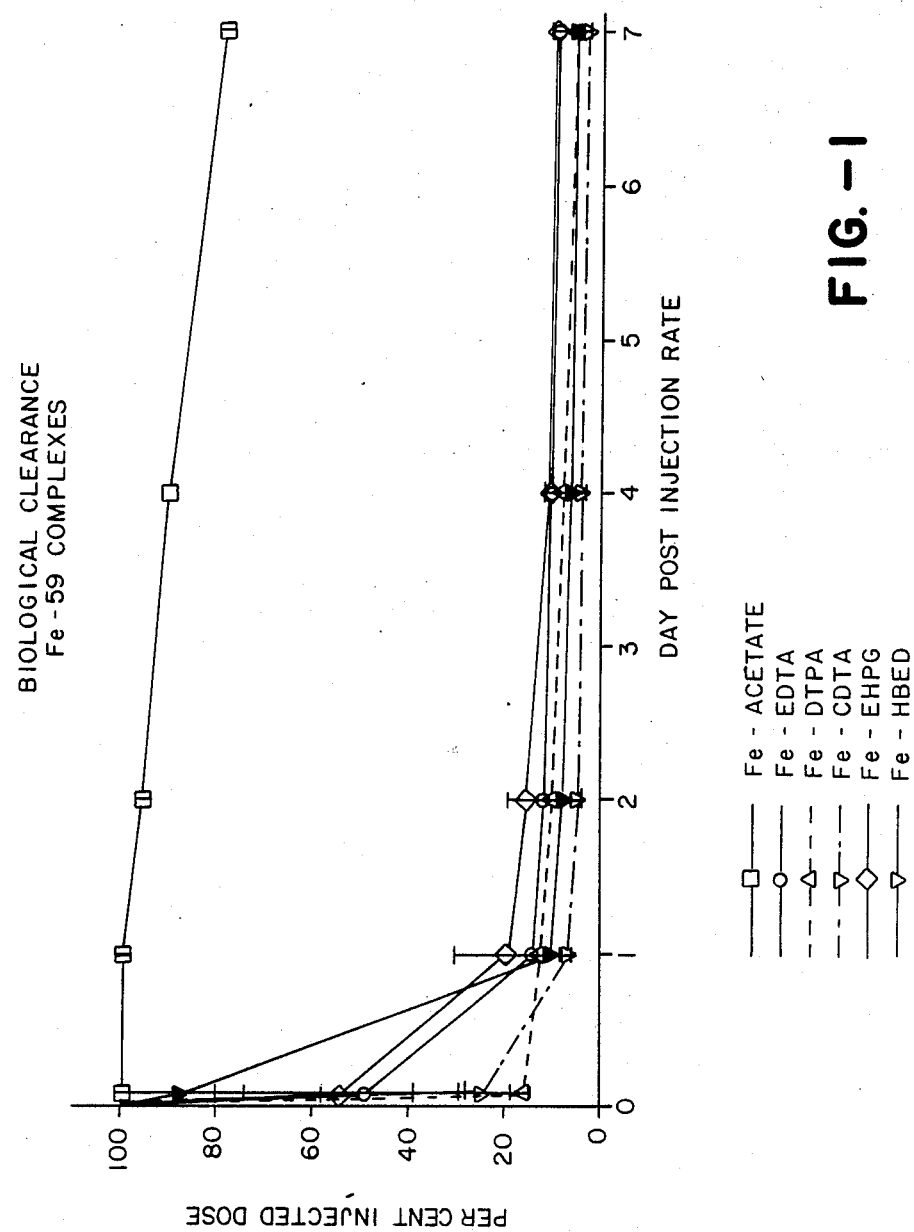
FIG. 1 is a graph of whole body biological clearance of rats injected by Fe-59 contrast agents.

The present invention is detected to a method for increasing the emitted signal, and thus obtaining in vivo differentiation of tissues, in an organism by NMR imaging, by administering as a contrast medium a chelated paramagnetic metal ion. In particular, the paramagnetic metal ion is a paramagnetic electronic form of iron. The chelators for these paramagnetic metal ions are organic chelating agents which are excretable by mammals. A particularly preferred class of chelators includes N,N'-bis(2-hydroxybenzyl)ethylenediamine-N,N'-diacetic acid (HBED) and ethylenebis-N,N'-(o-hydroxyphenylglycine) (EHPG), which are advantageous because of their hepatobiliary route of excretion from mammals. Another class of chelators includes desferrioxamine, diethylenetriaminepenaaacetic acid, glucoheptonic acid and phytate.

Exemplary chelators include, but are not limited to the following:

--- desferrioxamine,
diethylenetriamino-pentaacetic acid,
glucoheptonic acid,
phytate,
2,3-dihydroxybenzoic acid,
N—(2,3-dihydroxy-4-carboxybenzoyl)
desferrioxamine B,
N,N',N"—tris(2,3-dihydroxy-4-sulfobenzoyl)-
1,5,10-triazadecane,
N,N',N"—tris(2,3-dihydroxy-4-carboxy-
benzoyl)-1,5,10-triazadecane,
N,N',N",N"'—Tetrakis(2,3-dihydroxy-5-sulfobenzoyl)-
1,5,10,14-tetraazadecane,
N,N',N"'—Tris(2,3-dihydroxybenzoyl)-
1,3,5-triaminomethyl benzene,
N,N',N"—Tris(2,3-dihydroxy-5-sulfobenzoyl)-
1,3,5-triaminomethylbenzene,
N,N'—Bis(2,3-dihydroxybenzoyl)-1,4-diaminohexane,
N,N'—Bis(2,3-dihydroxybenzoyl)-1,6-diaminohexane,
N,N'—Bis(2,3-dihydroxybenzoyl)-1,8-diaminohexane,
N,N'—Bis(2,3-dihydroxybenzoyl)-1,10-diaminohexane,
N,N'—Bis(2,3-dihydroxybenzoyl)-1,12-diaminohexane,
N,N'—Bis(2-hydroxybenzyl)ethylenediamine
-N,N'—diacetic acid,
ethylenebis-N,N'—(o-hydroxyphenylglycine).

---

A particularly advantageous feature of two preferred contrast agents, Fe(EHPG) and Fe(HBED), is that NMR contrast enhancement is achieved at dose lower than known NMR contrast agents. Typically, NMR contrast agents, such as nitroxide free radicals, are utilized in dosages of 100 mg contrast agent per 100 gm weight of the animal. However, use of Fe(EHPG) or Fe(HBED) achieves contrast enhancement at doses as low as 1 mg contrast agent per kilogram weight of the animal.

Another particularly advantageous feature of the two above preferred contrast agents is their hepatobiliary method of excretion from the bodies of mammals. As a contrast agent the hepatobiliary route of excretion is characterized first by localization after administration in the liver, then concentration in the gall bladder. Concentration of the agent is then increased in the small intestine as the contents of the gall bladder are emptied, an then passed there to the large intestine.

Conventional pharmaceutically acceptable derivatives of the chelators may also be utilized, such as the hydrates, salts and N or O-acylated derivatives. In particular, derivatives such as the monohydrate, hydrochloride, methanesulfonate and N-acetylated compounds may be utilized.

The methods of formation of chelated paramagnetic metal ions is generally known. For example, stoichiometric amounts of the metal ion and the chelator may be admixed in a solution with an appropriate adjustment of pH, if necessary. The chelated metal ion may be isolated by conventional methods such as crystallization, chromatography, and the like, and admixed with conventional pharmaceutical carriers suitable for pharmaceutical administration.

The contrast agents according to the present invention may be used for imaging the circulatory system, the genitourinary system, hepatobiliary system and central nervous system, or for imaging tumors and abscesses in general. Contrast agents according to the present invention may also be useful to improve lesion detectability by NMR enhancement of either the lesion or adjacent normal structures.

The chelated metal ions may also be used in a conjugated form, i.e., conjugated with biomolecule. For example, the chelated paramagnetic metal ions may be conjugated to proteins such as tumor-specific monoclonal antibodies or to proteins such as albumin.

The contrast agents according to the present invention may be administered by any suitable method for introducing the contrast agent to the tissue area of interest. Preferably, the contrast agent may be introduced intravenously whereby dosages as low as 1 mg per kilogram weight of the animal are suitable to achieve contrast enhancements of the NMR image.

. TOXICITY

Solutions were prepared to evaluate the toxicity of the chelators and ferric complexes of the chelators.

A 1.2 M stock ferric solution was prepared by dissolving 32 g of $FeCl_3$* 6 $H_2O$ in 100 mL of 0.1 N HCl. It was standardized by EDTA titration using Variamine Blue B indicator.

A solution or suspension of 10 mmoles of each ligand in 20 mL of water was 70–80% neutralized by reaction with NaOH. The resulting solution (pH ~9) was added dropwise to a solution of 10.1 mmoles of $FeCl_3$ in 10 mL of water. The reaction mixture was adjusted to pH 7.0 with solid $NaHCO_3$ and stirred at 60°–80° C. for two hours. It then was ccentrifuged, and the supernatant was filtered through a 0.22 micron filter. Usually only a trace of ferric hydroxide precipitate was observed. Th filtrate was concentrated on a rotary evaporator, the pH adjusted to 7.0, and the volume adjusted to 20 mL. The Fe concentration (approximately 0.5 M) of this stock solution was determined by AA.

Tiron was obtained as the sodium salt. An aqueous 0.5 M solution was treated with a 2% excess of $FeCl_3$, and the reaction mixture was worked up as above.

A suspension of 3.6 g (10 mmoles) of EHPG in 15 mL of water was reacted with 17 mL of 2 N NaOH. The resulting dark yellow-orange solution was added dropwise to a solution of 2.7 g (1 mmoles) of FeCl$_3$* 6 H$_2$O in 10 mL of water. The reaction mixture was warmed to 60°-80° C. and held at that temperature for 2 hours. The thick orange-red suspension was diluted to 120 mL and heated to 90°-100° C. The hot suspension was filtered through filter aid, and the filtrate was allowed to cool to room temperature. After standing at 4° C. overnight, the chelate crystallized as a dark red solid, yield 2.75 g (44% of theory). UV-Vis: 480 (4700).

Fe-HBED was prepared as Fe-EHPG, above. Rather than crystallizing the product, the pH of the reaction mixture was adjusted to 7.0 with NaHCO$_3$ and filtered. The filtrate was used for subsequent experiments after appropriate volume adjustments and Fe determination. UV-VIS: 484 (2600).

For each compound at each dose, five normal BALB/C mice weighing 19-22 g were treated with test solution by injection into the tail vein. The injection volumes were approximately 0.2 mL. The behavior and condition of the mice were monitored for 1 week. The results are shown in Table I.

TABLE I

| COMPOUND | TOXICITY DATA[a] | | |
|---|---|---|---|
| | LD-0 (b) | ~LD-50 | LD-100 (c) |
| SALINE | 5 | 10 | 15 |
| Fe—HBED | 1.2 | | (d) |
| Fe—EHPG | 0.9 | | (d) |
| Fe—DF | 0.5 | | 2 (e) |
| (e) | | | |
| Fe—CDTA | — | 0.5 | 2 |
| DF | 0.5 | | 1 |
| Fe—DTPA | 0.5 | | — |
| Fe—EDTA | 0.5 | | — |
| CDTA | 0.05 | — | 0.5 |
| Fe—EDDA | — | | 0.5 |
| Fe—HEDTA | — | | 0.5 |
| Fe—NTA | — | | 0.5 |
| Fe—Tiron | — | | 0.5 |
| Fe—TTHA | — | | 0.5 |

[a] Compounds are listed in descending order of LD-0. Doses are expressed in units of mmoles/kg. Approximately isotonic aqueous solutions of agents were injected (volume: 0.2 mL) i.v. into tail veins of BALB/C mice. Five animals were used in each dose group.
[b] "LD-0" is the maximum dose at which no mortality was observed for seven days post injection.
[c] "LD-100" is the minimum dose for which 100% mortality was observed for seven days post injection.
[d] The maximum dose possible for bolus injection was limited by solubility. No mortality was observed.
[e] The line represents the minimum acceptable toxicity. LD-50 = 1 mmole/kg.

The following ligands were obtained from Aldrich Chemical Co.: nitrilotriacetic acid (NTA), ethylenediaminediacetic acid (EDDA), ethylenediaminetetraacetic acid (EDTA), N-(2-hydrosyethyl-)ethylene-diaminetriacetic acid (HEDTA), diethylene-triaminepentaacetic acid (DTPA), trans-1,2-cyclohexanediaminotetraacetic acid (CDTA), triethylenetetraamine-hexaacetic acid (TTHA), catechol-3,5-disulfonic acid disodium salt (Tiron). Ethylenebis-N,N'-(o-hydroxyphenylglycine) (EHPG) was obtained from Sigma Chemical Co. Ethylene bis(o-hydroxyphenyl)ethylenediaminediacetic acid (HBED) was purchased from Strem Chemical Co. Desferrioxamine B ("Desferal," abbreviated DF) was a CIBA product.

BODY CLEARANCE AND ORGAN DISTRIBUTION $^{59}$Fe was obtained as 0.06 M FeCl$_3$ in 0.5 N HCl; the specific activity was approximately 20 mCi/mmole (1.2 mCi/mL). Labeled commmplexes were preared by treating in a Teflon vial 10 uL of $^{59}$FeCl$_3$ with 25 uL of 2.0×10$^{-2}$ M solution of ligand, followed by 0.25 mL of 0.36 M, pH 7.3 Na HEPES buffer and 0.74 mL of water. The reaction mixture was held at 80° C. for 2 hours and then treated with 0.2 mL of 0.12 M solution of Fe-ligand complex. The resulting solution was filtered through a 0.22 u filter. A 0.2 mL dose contained 0.004 mmole of Fe-chelate with 2 uCi of $^{59}$Fe. $^{59}$Fe acetate was prepared as above, but without addition of unlabeled carrier Fe acetate.

For each complex shown in FIG. 1, a group of five BALB/C mice were treated as above with 0.2 mmole/Kg of labeled Fe-complex containing approximately 2 uCi of $^{59}$Fe. The animals were counted immediately after injection and at 2 hours, 1, 2, 4, and 7 days. Whole body counts were obtained using a Nuclear Chicago Tobor chamber gamma counter. Raw counts were background-subtracted and back-decayed to t$_0$, the time of injection. An $^{59}$Fe standard and background were counted at each time point. The results are shown in FIG. 1.

Figure 2:
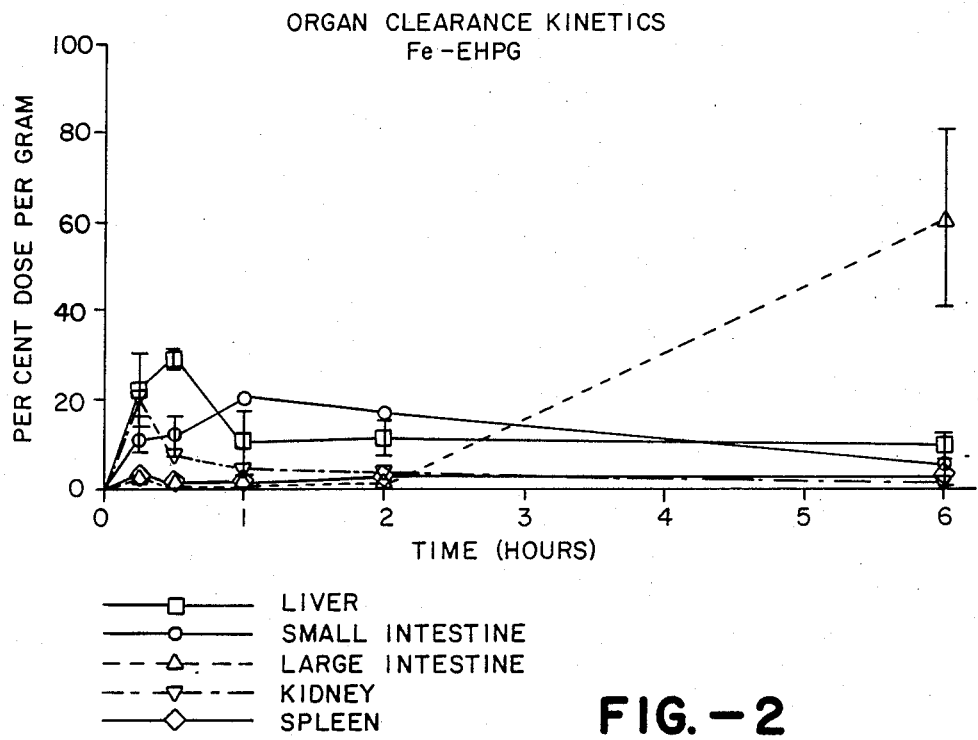
FIGS. 2 and 3 are graphs of organ clearance kinetics by rats injected by Fe-59 contrast agents.
Figure 3:
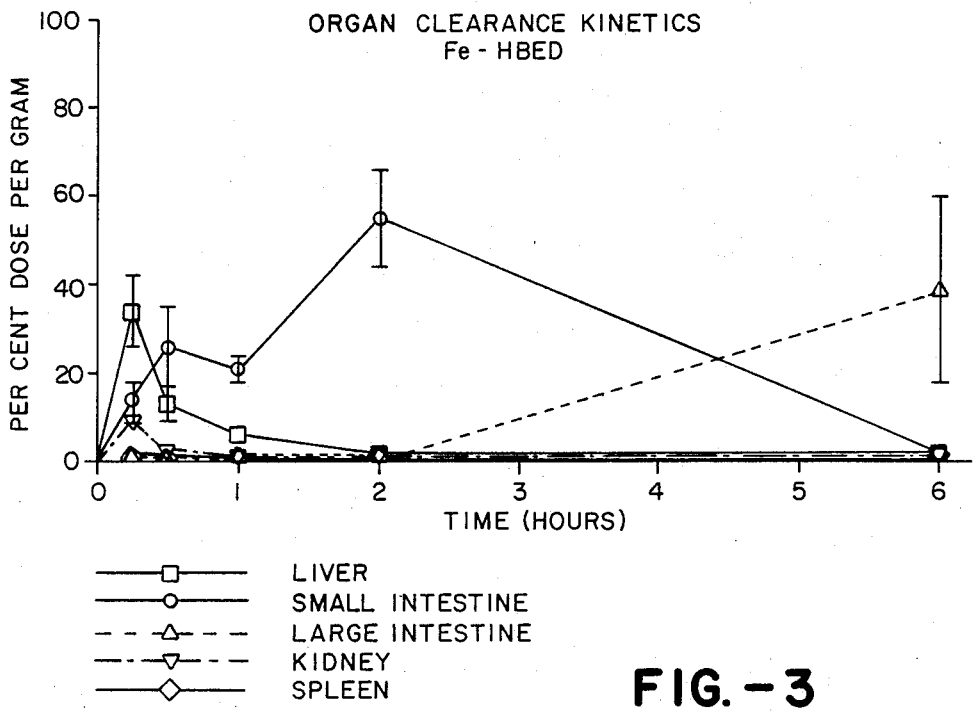

A group of three mice for Fe(HBED) and Fe(EHPG) at each time point (0.5 hr., 1 hr., 2 hr., 6 hr., 1, 2, 4, and 7 days) were treated as in the whole body clearance study above. After the appropriate time period, the animals were sacrificed and dissected. Organ weights were measured, and the organs were counted in a gamma counter. Due to its small size, the gall bladder was combined with the small intestine for weighing and counting. An $^{59}$Fe standard was also counted at each time point. Raw counts were background-subtracted and back-decayed to t$_0$, the time of injection. Activity was computed as a fraction of injected dose per gram of tissue. The results are shown in FIGS. 2 and 3. In each case liver levels were initially high and then decreased monotonically. Fe-HBED appeared to have reached a maximum in the liver earlier than Fe-EHPG. The small intestine (which was combined with gall bladder for weighing and counting) values were initially low, rose to a maximum at about 1-2 hours, and then decreased out to 6 hours. Finally, the large intestine levels, representing both gut tissue and contents, started and remained lower than the liver or small intestine values up to the 2 hour time point; at the final time of 6 hours, they exceeded all of the other values.

These results are consistent with a hepatobiliary route of excretion in which the complexes were first localized in the liver and then concentrated in the gall bladder. The contents of the gall bladder were then emptied into the small intestine and passed from there to the large intestine.

MAGNETIC RESONANCE IMAGING

Imaging tests were performed on a General Electric CSI-II 2 Tesla (85.6 MHz proton resonant frequency) chemical shift imaging-spectrometer (GE Medical Systems,Inc., Fremont, CA). A standard 2-Dimensional Fourier Transform (2DFT) spin warp sequence with 2 mm slice thickness and 128 phase-encoding cycles by 512 complex (quadrature detected) data points was used. These were transposed to 512×512 image output pixels (256 level gray scale) over a 140×150 field of view. Coronal spin echo images were obtained using a TR of 300 msec, a TE of 14 msec, and averaging four acquisitions per cycle. The RF coil used was a homebuilt distributed capacitance (low-pass birdcage) design coupled to balanced-matched RF input circuitry.

Experiments were typically run simultaneously on two 20 g BALB/C mice. These were anesthetized i.p. with ketamine, and a 27 G catheter was inserted into the tail vein and connected to a 0.5 cc syringe containing contrast agent. The mice were placed side-by-side and supine in a holder within the RF coil, and a precontrast image was obtained. Contrast agent then was administered, and then post contrast images were obtained in registration at designated time intervals.

The images demonstrated the difference in biodistribution of the hepatobiliary agents Fe-EHPG and Fe-HBED compared to other agents. The organ distribution indicated by the radiolabeling experiments was confirmed by MRI. Both Fe(EHPG) and Fe(HBED) first concentrate in the liver, while the gall bladder remains unenhanced. Contrast agent then begins to collect in the gall bladder, and it gradually becomes brighter than the surrounding liver. The final images in each series were acquired 50 minutes post-contrast and indicate that the liver intensity has decreased, while the gall bladder contrast remains markedly high.

In contrast to FE-EHPG and FE-HBED, Fe-DF and GD-DTPA give rise only to a small increase in signal intensity in the liver and essentially none in the gall bladder. All four of these agents are concentrated in the urinary bladder.

What is claimed is:

1. A method of obtaining in vivo differentiation of tissues in the hepatobiliary system of an animal by nuclear magnetic resonance imaging comprising the steps of introducing into said tissues a metal complex of paramanetic iron and a chelator, said complex being excretable through said hepatobiliary system of said animal; and observing a nuclear magnetic image of said tissues, wherein said chelator is selected from the group consisting of N,N'-bis(2-hydroxybenzyl)ethylendiamine-N,N'-diacetic acid and ethylenebis-N,N'-(o-hydroxyphenylglycine).

2. A method according to claim 1 wherein said chelator comprises N,N'-bis(2-hydroxybenzyl) ethylenediamine-N,N'-diacetic acid.

3. A method according to claim 1 wherein said chelator comprises ethylenebis-N,N'-(o-hydroxyphenylglycine).

4. A method according to claim 1 wherein said complex is conjugated with a biomolecule.

* * * * *

UNITED STATES PATENT AND TRADEMARK OFFICE
Certificate

Patent No. 4,909,257                                    Patented: March 20, 1990

On petition requesting issuance of a certificate for correction of inventorship pursuant to 35 U.S.C. 256, it has been found that the above-identified patent, through error and without any deceptive intent, improperly sets forth the inventorship. Accordingly, it is hereby certified that the correct inventorship of this patent is: Barry L. Engelstad Signed and Sealed this Twenty-Eighth Day of May, 1991.

C. FRED ROSENBAUM

*SPE Art Unit 336*